Figure 1:
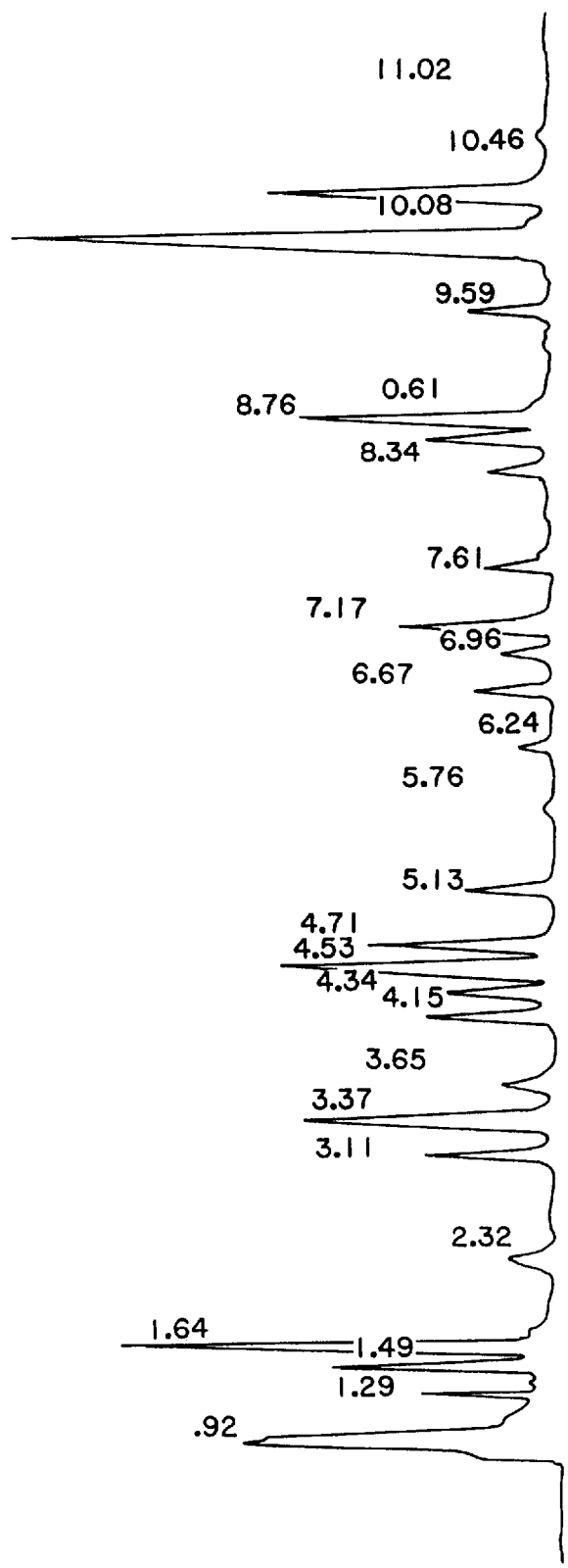

United States Patent [19]
Vandenbergh et al.

[11] Patent Number: 5,877,272
[45] Date of Patent: Mar. 2, 1999

[54] **BACTERIOCIN FROM *LACTOCOCCUS LACTIS***

[75] Inventors: Peter A. Vandenbergh, Sarasota; Shirley A. Walker; Blair S. Kunka, both of Bradenton, all of Fla.

[73] Assignee: Microlife Technics, Inc., Sarasota, Fla.

[21] Appl. No.: 806,224

[22] Filed: Dec. 13, 1991

Related U.S. Application Data

[62] Division of Ser. No. 492,969, Mar. 13, 1990, abandoned.

[51] Int. Cl.⁶ .................................................. C07K 14/195
[52] U.S. Cl. ........................... 530/300; 435/128; 435/713
[58] Field of Search ............................ 530/300; 435/128, 435/71.3

[56] References Cited

PUBLICATIONS

Klaenhammer, T.R., Biochemie 70: 337–349 (1988).
Eapen, K.C., et al., J. Fd. Sci. Technol. 20: 231–240 (1983).
Davey, G.P. and B.C. Richardson., Appl. Environ. Microbiol. 41: 84–89 (1981).
Kozak, W., et al., J. Dairy Res. 45:247–257 (1978).
Geis, A., et al., Appl. Environ. Microbiol. 45: 205–211 (1983).
Bhunia, A.K. et al, Appl. Bacteriol 65: 261–268 (1988).
Mundt, M.O., W.G. Beattie, and F.R. Wieland, J. Bacteriol, 98: 938–942 (1969).
The Van Nostrand Chemist's Dictionary, D. Van Nostrand Company Inc., New York, 1953, p. 385.

*Primary Examiner*—Marian C. Knode
*Attorney, Agent, or Firm*—Ian C. McLeod

[57] ABSTRACT

A bacteriocin produced by *Lactococcus lactis* NRRL-B-18535 is described. The bacteriocin is useful in foods and other materials and has a wide spectrum of activity against Gram-positive bacteria in a pH range between 2 and 8.

1 Claim, 1 Drawing Sheet

5,877,272

BACTERIOCIN FROM *LACTOCOCCUS LACTIS*

This is a divisional of application Ser. No. 07/492,969 filed on Mar. 13, 1990, now abandoned.

BACKGROUND OF THE INVENTION

1. Field of the Invention

The present invention relates to a novel bacteriocin derived from a Lactococcus and method of use to inhibit bacteria, particularly in foods and other materials in need of protection from the bacteria. The present invention particularly relates to a bacteriocin produced by *Lactococcus lactis* LL-1 deposited as NRRL-B-18535 (previously known as *Streptococcus lactis*).

2. Prior Art

The lactic streptococci have been previously described to produce a variety of polypeptide antibiotics, diplococcin, lactostrepcins and bacteriocins (Klaenhammer, T. R., Biochemie 70: 337–349 (1988)). The term nisin describes a family of polypeptide antibiotics produced by *Lactococcus lactis* that prevents the outgrowth of Clostridium and Bacillus spores (Eapen, K. C., et al., J. Food. Sci. Technol. 20: 231–240 (1983)). Bacteriocins are also produced by pediococci.

Diplococcin is an antimicrobial agent produced by *Lactococcus cremoris*. This inhibitor does not inhibit sporeformers and is only active against other dairy lactococci (Davey, G. P. and B. C. Richardson., Appl. Environ. Microbiol. 41:84–89 (1981)).

Lactostrepcins are inhibitory proteins produced by the lactococci that inhibit other streptococci. These molecules are active at relatively low pH and activity is completely lost when the pH is raised to 7.0 (Kozak, W., et al., J. Dairy Res. 45: 247–257 (1978)).

Bacteriocins produced by lactic lactococci have been observed in many commercial strains (Geis, A., et al., Appl. Environ. Microbiol. 45:205–211 (1983)). Eight bacteriocin types (I–VIII) have been identified on the basis of their activity spectrum, proteolytic enzyme susceptibility, heat stability and cross-reaction with other bacteriocin producers (Geis, A., et al. Appl. Environ. Microbiol. 45:205–211 (1983)).

The problem is that the bacteriocins are not active over a wide pH range. It would be very desirable to provide a bacteriocin which is useful in a wide variety of foods regardless of whether they are acidic or basic.

OBJECTS

It is therefore an object of the present invention to provide a novel bacteriocin which is effective at a pH between pH 2 and 8. It is further an object of the present invention to provide a bacteriocin which can be relatively easily isolated from a particular strain of *Lactococcus lactis*. These and other objects will become increasingly apparent by reference to the following description and the drawings.

IN THE DRAWINGS

FIG. 1 is a high pressure liquid chromatographic (HPLC) amino acid profile of the bacteriocin of the present invention.

GENERAL DESCRIPTION

The present invention relates to a bacteriocin produced by a Lactococcus which comprises: a protein having a molecular weight of about 6000 daltons, which is inactivated by protease and not inactivated by alpha-chymotrypsin, trypsin, lipase, pepsin and lysozyme, inhibits the growth of bacteria selected from the group consisting of *Staphylococcus aureus, Staphylococcus epidermidis, Staphylococcus carnosus, Pediococcus pentosaceus, Pediococcus acidilactici, Lactococcus cremoris, Lactococcus lactis, Leuconostoc mesenteroides, Lactobacillus bulgaricus, Lactobacillus fermentum, Lactobacillus bifermentans* and *Lactobacillus plantarum* and has an optimal pH for inhibition between about pH 2 and 8.

Further the present invention relates to a method for inhibiting Gram-positive bacteria which can occur with a material which comprises: providing a bacteriocin with the material in an effective amount which inhibits the Gram-positive bacteria, wherein the bacteriocin is derived from a *Lactococcus lactis* and wherein the bacteriocin is a protein having a molecular weight of about 6000 daltons, is inactivated by protease and not inactivated by alpha-chymotrypsin, trypsin, lipase, pepsin and lysozyme, inhibits the growth of bacteria selected from the group consisting of *Staphylococcus aureus, Staphylococcus epidermidis, Staphylococcus carnosus, Pediococcus pentosaceus, Pediococcus acidilactici, Lactococcus cremoris, Lactococcus lactis, Leuconostoc mesenteroides, Lactobacillus bulgaricus, Lactobacillus fermentum, Lactobacillus bifermentans* and *Lactobacillus plantarum* and has an optimal pH for inhibition between about pH 2 and 8.

Further the present invention relates to a composition which comprises: an unspoiled food system which is spoiled by Gram-positive bacteria and a bacteriocin derived from cells of a *Lactococcus lactis*, wherein the composition contains an amount of the bacteriocin to provide between about 10 and 100,000 AU of the bacteriocin per gram of the food system sufficient for the bacteriocin to inhibit the Gram-positive bacteria and wherein the bacteriocin is a protein having a molecular weight of about 6000 daltons, is inactivated by protease and not inactivated by alpha-chymotrypsin, trypsin, lipase, pepsin and lysozyme, inhibits the growth of bacteria selected from the group consisting of *Staphylococcus aureus, Staphylococcus epidermidis, Staphylococcus carnosus, Pediococcus pentosaceus, Pediococcus acidilactici, Lactococcus cremoris, Lactococcus lactis, Leuconostoc mesenteroides, Lactobacillus bulgaricus, Lactobacillus fermentum, Lactobacillus bifermentans* and *Lactobacillus plantarum* and has an optimal pH for inhibition between about pH 2 and 8.

Further the present invention relates to a device which comprises: a material on the device which can become infected with Gram-positive bacteria, and a bacteriocin provided with the material in an amount sufficient to inhibit the Gram-positive bacteria, wherein the bacteriocin is from cells of a *Lactococcus lactis* and is a protein having a molecular weight of about 6000 daltons, is inactivated by protease and not inactivated by alpha-chymotrypsin, trypsin, lipase, pepsin and lysozyme, inhibits the growth of *Staphylococcus aureus, Staphylococcus epidermidis, Staphyloco-* cus carnosus, Pediococcus pentosaceus, Pediococcus acidilactici, Lactococcus cremoris, Lactococcus lactis, Leuconostoc mesenteroides, Lactobacillus bulgaricus, Lactobacillus fermentum, Lactobacillus bifermentans and Lactobacillus plantarum and has an optimal pH for inhibition between about pH 2 and 8.

Further the present invention relates to a method for producing a bacteriocin which comprises: incubating live cells of a Lactococcus lactis in a growth medium for the cells so as to produce the bacteriocin in the growth medium, and wherein the bacteriocin is a protein having a molecular weight of about 6000 daltons, is inactivated by protease and not inactivated by alpha-chymotrypsin, trypsin, lipase, pepsin and lysozyme, inhibits the growth of bacteria selected from the group consisting of Staphylococcus aureus, Staphylococcus epidermidis, Staphylococcus carnosus, Pediococcus pentosaceus, Pediococcus acidilactici, Lactococcus cremoris, Lactococcus lactis, Leuconostoc mesenteroides, Lactobacillus bulgaricus, Lactobacillus fermentum, Lactobacillus bifermentans and Lactobacillus plantarum and has an optimal pH for inhibition between about pH 2 and 8.

The strain Lactococcus lactis LLA 1.0 has been deposited under the Budapest Treaty with the Northern Regional Research Laboratory in Peoria, Ill. as NRRL-B-18535. It is available only upon request by name and deposit number. The strain has the following fermentation characteristics: it is able to ferment dextrose, mannitol, sucrose, maltose, salicin, rhamnose, trehalose, cellobiose, mannose, fructose and N-acetyl-glucosamine.

The strain had three resident plasmids measuring about 33.42, 28.57 and 5.82 Mdal in size.

SPECIFIC DESCRIPTION

The following Examples show the production of the bacteriocin from Lactococcus lactis NRRL-B-18535 and its use in foods and other materials. It also shows the amino acid profile of a hydrolyzate of the bacteriocin. The determination of the approximate molecular weight is also shown.

EXAMPLE 1

Production of the Bacteriocin
Bacterial Strains and Media

The bacterial strains used in this study were routinely grown on MRS lactobacillus broth (Difco, Detroit, Mich.).
Bacteriocin Assay Production of bacteriocin was assayed by spotting cells on MRS agar (Difco Laboratories, Detroit, Mich.) that contained 2.0% MES ([N-morpholino] ethanesulfonic acid buffer; Sigma, St. Louis, Mo.). These plates were incubated at 35° C. for 18 hours. Assay plates were exposed to chloroform vapor for 30 minutes and overlaid with soft agar (0.075%) seeded with indicator cells. Plates were incubated at 32° C. for 18 hours. Isolates producing a clear zone were considered as producing bacteriocin.
Inhibitory Spectrum of LL-1

The plate assay system was used to evaluate the spectrum of bacteriocin activity. The strain NRRL-B-18535 showed activity against strains of Staphylococcus aureus, S. epidermidis, S. carnosus, Pediococcus pentosaceus, P. acidilactici, Lactococcus cremoris, Lactococcus lactis, Lactobacillus fermentum, Lactobacillus bifermentans, Leuconostoc mesenteroides, Lactobacillus bulgaricus and L. plantarum. Strains of Streptococcus mutans, S. sanguis, S. faecalis and Listeria monocytogenes were not sensitive to the bacteriocin LL-1. The strain was resistant to nisin.

EXAMPLE 2

Purification and Characterization of the Bacteriocin

One liter of MRS broth (Difco) was inoculated at 1% with an 8 hour old culture of LLA 1.0 grown in the medium of Example 1 and was incubated statically at 32° C. for 24 hours. After 24 hours the cells were removed by centrifugation at 16,000×g for 20 minutes at 4° C. The supernatant was filtered through a 0.22 micron (pore size) filter (Millipore Corp., Bedford, Mass.). The supernatant was assayed for bacteriocin activity by spotting 5 microliters of a serial two-fold dilution series onto MRS plates overlaid with soft agar seeded with indicator cells. Assay plates were incubated at 35° C. The indicator strain was Pediococcus pentosaceus FBB63C. One arbitrary unit (AU) of bacteriocin was defined as 5 microliters of the highest dilution of culture supernatant yielding a definite zone of growth inhibition on the indicator lawn. The titer was expressed as the reciprocal of the highest dilution showing inhibition.

Ammonium sulfate (Sigma Chemical Co., St. Louis, Mo.) was added to the filtered supernatant to 50% (wt/vol) saturation at 4° C. After precipitation for 18 hours at 4° C., the mixture was centrifuged at 16,000×g for 15 minutes at 4° C. The precipitate was reconstituted in 25 ml of 0.05M sodium citrate buffer, pH 6.0. The reconstituted precipitate was dialyzed against the 0.05M sodium citrate buffer at 4° C. by using Spectra/Por no. 6 membrane tubing (Spectrum Medical Industries, Inc., Los Angeles, Calif.) and the titer of its activity was determined. The reconstituted dialyzed precipitate was then subjected to further purification with gel filtration chromatographs using Spectra/Gel AcA202 (Spectrum Medical Industries, Inc., Los Angeles, Calif.).

The bacteriocin preparation (6 ml) was applied to an ascending Spectra/Gel AcA 202 column (2.6 by 30 cm) in 0.05M sodium citrate buffer (pH 6.0). Fractions were collected (4 ml) and assayed for bacteriocin activity. The active factors were then collected and concentrated 10-fold in the dialysis tubing by the removal of water with Carbowax 20 (Fisher Scientific Co., Pittsburgh, Pa.). This active concentrated fraction was then applied to an ascending Spectra/Gel AcA 202 column (1.6 by 60 cm) in 0.05M sodium citrate buffer (pH 6.0). The titer of the partially purified bacteriocin was determined and was used for partial characterization of the bacteriocin.
Effects of Heat Treatment and Enzymes A partially purified sample of bacteriocin LL-1 (6,400 AU/ml) was assayed for thermostability and enzymatic effects on activity. The bacteriocin was incubated with each enzyme at a final concentration of 50 micrograms/ml for 60 minutes. Incubation in the presence of alpha-chymotrypsin and trypsin was at 25° C., and all other enzyme-bacteriocin mixtures were incubated at 37° C. Inactivation of the enzymes was achieved by boiling them for 3 minutes. It is considered to be a type VI bacteriocin because the strain that produces it is resistant to nisin and does not inhibit *S. sanguis*. Temperature stability of the bacteriocin was assessed by heating a solution of bacteriocin to 80° C. for 60 minutes, 100° C. for 10 minutes, and 121° C. for 15 minutes. After each treatment, bacteriocin samples were assayed for activity.

Enzymes

All enzymes were obtained from Sigma. Alpha-chymotrypsin (type II; 47 U/mg) and lipase (type 1; 8.6 U/mg) were dissolved in 0.05M Tris hydrochloride (pH 8.0) containing 0.01M $CaCl_2$; protease (type V; 1 U/mg), lysozyme (grade I, 41, 400 U/mg) and trypsin (type IX; 15,000 U/mg) were dissolved in 0.05M Tris hydrochloride (pH 8.0); and pepsin (3,200 U/mg) was dissolved in 0.2M citrate buffer (pH 6.0).

pH Stability of Activity

Partially purified bacteriocin (1 ml) was dialyzed against buffers of various pH's. The bacteriocin solution (12,800 AU/ml) was dialyzed for 18 hours with 2 changes against 0.05M glycine hydrochloride buffer (pH 2.0), 0.05M citrate buffer (pH 3 to 6), 0.05M Tris hydrochloride (pH 7 to 9), and 0.05M carbonate-bicarbonate buffer (pH 10 to 11). After dialysis, the contents of the tubing were assayed for bacteriocin activity. The bacteriocin LL-1 was sensitive to protease and not sensitive to alpha-chymotrypsin, trypsin, lipase, pepsin or lysozyme. The bacteriocin was observed to be most stable from pH 2–8, with some loss in activity at pH 9 and 10. Approximately one-fourth of the activity was still present at pH 11.0. Exposure of the bacteriocin to 121° C. did destroy all of the LL-1 activity. Boiling at 100° C. for 10 minutes resulted in 75% loss in activity of the bacteriocin. This 75% activity loss was also observed at 80° C. for 60 minutes.

EXAMPLE 3

Nutritional Studies

Each of the media listed in Table 1 was prepared in 100 ml quantities.

The media were adjusted to pH 6.8 before autoclaving. The media were inoculated with an 8 hour culture of NRRL-B-18535 at a rate of 1% and then incubated at 32° C. for 24 hours. After 24 hours, 25 ml of the above culture was centrifuged at 24,000×g for 15 minutes at 4° C. The supernatant was then filter sterilized using a 0.22 micron filter (Millipore, Bedford, Mass.) and tested for the least titer which inhibited *Pediococcus pentosaceus* FBB63C as the indicator strain.

The results of the nutritional study are depicted in Table 1.

TABLE 1

Nutritional Studies of NRRL-B-18535 for the Production of Bacteriocin LL-1.

| Media | Titer |
|---|---|
| Brain Heart Infusion Broth (Difco, Detroit, MI) | 0 |
| Tryptic Soy Broth (Difco, Detroit, MI) | 0 |
| All Purpose Tween Broth (Difco, Detroit, MI) | 1:2+ |
| MRS Lactobacillus Broth (Difco, Detroit, MI) | 1:8 |

TABLE 1-continued

Nutritional Studies of NRRL-B-18535 for the Production of Bacteriocin LL-1.

| Media | | Titer |
|---|---|---|
| MRS + 1% yeast extract (Oxoid, Basingstoke, England) | | 1:4+ |
| MRS + 1% Hy-Soy ™ (Sheffield Products, Norwich, NY) | | 1:8 |
| MRS + 1% Hy-Case ™ (Sheffield Products, Norwich, NY) | | 1:8 |
| 10% peptonized milk with 1% glucose | | 0 |
| 10% peptonized whey with 1% glucose | | 0 |
| Corn Steep Base (I) | | |
| 4% cornsteep | | |
| 3% yeast extract | | |
| 5% glucose with: | | |
| (a) | Nothing | 1+ |
| (b) | 1% N-Z Amine Type AS ™ (Sheffield Products, Norwich, NY) | 1+ |
| (c) | 1% PRIMATONE SGM ™ (Sheffield Products, Norwich, NY) | 1+ |
| (d) | 1% EDAMIN K ™ (Sheffield Products, Norwich, NY) | 1 |
| (e) | 1% PRIMAGEN P ™ (Sheffield Products, Norwich, NY) | 1:2 |
| (f) | 1% PRIMATONE HS ™ (Sheffield Products, Norwich, NY) | 1:2 |
| (g) | 1% EDAMIN S ™ (Sheffield Products, Norwich, NY) | 1+ |
| (h) | 1% AMICASE T ™ (Sheffield Products, Norwich, NY) | 1:2 |
| (i) | 1% AMICASE ™ (Sheffield Products, Norwich, NY) | 1:2 |
| (j) | 1% PRIMATONE ™ (Sheffield Products, Norwich, NY) | 1:2 |
| (k) | 1% AMISOY ™ (Sheffield Products, Norwich, NY) | 1:2+ |
| (l) | 1% HYSOY TYPE T ™ (Sheffield Products, Norwich, NY) | 1 |
| (m) | 1% PRIMATONE G ™ (Sheffield Products, Norwich, NY) | 1:2 |
| (n) | 1% PRIMAGEN ™ (Sheffield Products, Norwich, NY) | 1:2+ |
| CORN STEEP BASE (II) | | |
| 4% cornsteep | | |
| 5% dextrose, with: | | |
| (a) | 2% AMISOY ™ | 1:2 |
| (b) | 2% PRIMAGEN ™ | |

The most effective medium for the production of bacteriocin LL-1 appears to be MRS broth that is unsupplemented. Other media were not as effective and protein hydrolysate supplements did not stimulate bacteriocin production. Whey or milk based media were the least effective for the production of LL-1.

EXAMPLE 4

Production of Dried Bacteriocin LL-1

*Lactococcus lactis* NRRL-B-18535 was grown in one liter of MRS broth (Difco, Detroit, Mich.) for 24 hours at 32° C. The cells were pelleted by centrifugation at 16,000×g at 4° C., and the supernatant was collected. The supernatant was then filter sterilized with a 0.22 micron pore size filter. Nonfat dry milk powder was added to 10% (weight/volume) to facilitate drying. This mixture was lyophilized into a dry powder.

EXAMPLE 5

Minimum Inhibitory Concentration (MIC) of the Lyophilized Bacteriocin LL-1 Against *Pediococcus pentosaceus* FBB63C The bacteriocin LL-1 powder of Example 4 was dissolved in APT broth or Tryptic Soy Broth and two-fold serially diluted to concentrations ranging from 1000 AU/ml to 2.0 AU/ml. Approximately 1×10³ *Pediococcus pentosaceus*/ml were added to each of the tubes which were then incubated for 24 hours at 35° C. The MIC value was the lowest concentration tube displaying no visible turbidity. The results are summarized in Table 2.

TABLE 2

| Strain | MIC |
| --- | --- |
| Pediococcus pentosaceus | 8.0 AU/ml |

EXAMPLE 6

Minimum inhibitory concentration (MIC) of the lyophilizd bactriocin LL-1 against *Straphylococcus aureus* 265

The bacteriocin LL-1 powder of Example 4 was dissolved in APT broth or Tryptic Soy Broth and two-fold serially diluted to concentrations ranging from 1000 AU/ml to 2.0 AU/ml. Approximately 1×10³ *Staphylococcus aureus*/ml were added to each of the tubes which were then incubated for 24 hours at 35° C. The MIC value was the lowest concentration tube displaying no visible turbidity. The results are summarized in Table 3.

TABLE 3

| Strain | MIC |
| --- | --- |
| Staphylococcus aureus | 1000 AU/ml |

EXAMPLE 7

Molecular Weight Determination of the Bacteriocin LL-1

The molecular weight of the bacteriocin of Example 1 was determined by gel filtration. 1.5 ml (800 AU/ml) was applied to an ascending Spectra/Gel AcA 202 column (1.6 by 60 cm: Spectrum, Los Angeles, Calif.) in 0.05M sodium citrate buffer (pH 6.0). The elution volume of the bacteriocin was compared to the elution volumes of standard proteins. Bacteriocin activity was determined as described above. The protein standards and their molecular weights included the following: cytochrome C, 12,400; aprotinin, 6,500; melittin, 2,846 (Sigma).

The bacteriocin preparations were examined on 12% SDS-PAGE gel. Samples and molecular weight standards 1 mg/ml were dissolved in sample buffer and loaded on the gel. The material was then subjected to electrophoresis for 1 hour at 16 mA and then for 1 hour at 24 mA. The gel was then stained with silver strain (BioRad, Richmond, Calif.) or assayed for bcteriocin activity by a direct detection system (Bhunia, A. K. et al, Appl. Bacteriol. 65:261–268 (1988)).

The molecular weight was observed to be approximately 6,000 daltons from gel filtration. The SDS gel overlay with *Pediococcus pentsaceus* confirmed the approximate size observed with gel filtration.

EXAMPLE 8

Amino Acid Profile of Purified Bacteriocin LL-1

The bacteriocin was purified as previously described in Example 7. An active concentrated fraction from the Spectra/Gel AcA202 column was subjected to further purification using a C-8 analytical column. Fractions were assayed for bacteriocin activity. The active fractions were then further concentrated using the Speed Vac Concentrator™ (Savant Instruments Inc. Farmingdale, N.Y.) and resuspended in 50 microliters of distilled water. This material was then analyzed for amino acid content using a modification of the PICO-TAG™ system (Waters Associates, Milford, Mass.). The method involves sample hydrolysis followed by derivatization with phenylisothiocyanate and subsequent analysis by HPLC [Mundt, M. O., W. G. Beattie, and F. R. Wieland, J. Bacteriol. 98:938–942 (1969)]. Amino acids were identified by comparing the retention times of a known standard to that of the active fraction hydrolyzate (FIG. 1.) The results listed in Table 4 compare the ratios of the various amino acids observed to glutamic acid, which was observed in the greatest amount.

TABLE 4

Ratios of various amino acids to glutamic acid.

| Amino Acid | Ratio to glutamic acid |
| --- | --- |
| Aspartic acid | 0.42 |
| Glutamic acid | 1.0 |
| Serine | 0.35 |
| Glycine | 0.83 |
| Histidine | 0.16 |
| Arginine | 0.35 |
| Threonine | 0.34 |
| Alanine | 0.76 |
| Proline | 0.48 |
| Tyrosine | 0.19 |
| Valine | 0.43 |
| Methionine | 0.14 |
| Cysteine | 0.12 |
| Isoleucine | 0.27 |
| Leucine | 0.64 |
| Phenylalanine | 0.19 |
| Lysine | 0.50 |

EXAMPLE 9

Salad Dressing With Added Contaminant Microorganisms

The following Tables 5, 6 and 7 show the use of the bacteriocin LL-1 in salad dressing to which *Lactobacillus fermentum* NRRL-B-18586 has been added. The spoilage bacterium strain is one which is very active in food spoilage.

TABLE 5

| | Designation | Dressing[1] | Spoilage Bacteria[2] | LL-1[3] | Dilution Buffer[4] |
| --- | --- | --- | --- | --- | --- |
| Uninoculated Control | A | 100 g | 0 | 0 | 3.9 ml |
| Inoculated Control | B | 100 g | 0.1ml(10⁶) | 0 | 3.9 ml |
| Inoculated plus bacteriocin LL-1 (200 Au/g) | C | 100 g | 0.1ml(10⁶) | 0.78ml | 3.12ml |
| Inoculated plus bacteriocin | D | 100 g | 0.1ml(10⁶) | 3.9 ml | 0 |

TABLE 5-continued

| Designation | Dressing[1] | Spoilage Bacteria[2] | LL-1[3] | Dilution Buffer[4] |
|---|---|---|---|---|
| LL-1 (1000 AU/g) | | | | |

[1]Dressing used was Marie's ™ Ranch Dressing. The general composition of the salad dressing was soybean oil, fresh buttermilk, whole eggs, egg yolks, distilled vinegar, sugar, salt, spices, garlic, onion and xanthan gum.
[2]*Lactobacillus fermentum* NRRL-B-18586 streptomycin resistant, addition about $3.0 \times 10^3$ cfu/g of salad dressing.
[3]Bacteriocin LL-1 used was a 50% ammonium sulfate preparation that was dialyzed against 0.05M sodium citrate buffer (pH 6.0), then filter sterilized. (Concentration: 25,600 AU/ml). The experiment was conducted at 25° C. for ten days.
[4]The dilution buffer was used to provide equivalent volumes of added fluid.

TABLE 6

Bacterial counts in the Salad Dressing.

| Designation | Time (days) | | |
|---|---|---|---|
| | T-0[a] | T-1 | T-10 |
| A | <$10^{2b}$ | <$10^2$ | <$10^2$ |
| B | $4.0 \times 10^3$ | $3.1 \times 10^3$ | $7.0 \times 10^2$ |
| C | $3.0 \times 10^3$ | $2.2 \times 10^3$ | $2.5 \times 10^2$ |
| D | $2.3 \times 10^3$ | $3.5 \times 10^2$ | <$10^2$ |

[a]Time (days)
[b]Bacterial Counts (cfu/g) *Lactobacillus fermentum* 18586 Sm[r]

TABLE 7

Organoleptic Evaluation of Salad Dressing.

| Designation | T-10[a] |
|---|---|
| A | Not spoiled |
| B | Spoiled[b] |
| C | Not spoiled |
| D | Not spoiled |

[a]Time (days)
[b]Acetic acid was detected by smell and taste, and gas ($CO_2$) was produced and observed in the dressing as evidence of spoilage.

This Example shows that the bacteriocin LL-1 was effective to inhibit spoilage bacteria introduced into a salad dressing.

EXAMPLE 10

Salad Dressing With Natural Contaminant Microorganisms

The following Tables 8 and 9 demonstrate the inhibition of the normal, lactic acid spoilage flora using the bacteriocin LL-1 in salad dressing:

TABLE 8

| | Designation | Dressing[1] | LL-1[2] | Dilution Buffer |
|---|---|---|---|---|
| Uninoculated Control | A | 100 g | 0 | 3.9 ml |
| Uninoculated plus bacteriocin LL-1 (200 AU/g) | B | 100 g | 0.78ml | 3.12ml |

TABLE 8-continued

| | Designation | Dressing[1] | LL-1[2] | Dilution Buffer |
|---|---|---|---|---|
| Uninoculated plus bacteriocin LL-1 (1000 AU/g) | C | 100 g | 3.9ml | 0 |

[1]Dressing used was Marie's ™ Ranch Dressing. The general composition of the salad dressing was soybean oil, fresh buttermilk, whole eggs, egg yolks, distilled vinegar, sugar, salt, spices, garlic, onion and xanthan gum. Because of the natural ingredients there is a high level of lactic bacteria such as *Lactobacillus fermentum* NRRL-B-18586 in the salad dressing.
[2]Bacteriocin LL-1 used was a 50% ammonium sulfate preparation that was dialyzed against 0.05M sodium citrate buffer (pH 6.0), then filter sterilized. (Concentration: 25,600 AU/ml). The dilution buffer was used to provide equivalent volumes of added liquid with LL-1.
The experiment was conducted at 25° C. for ten days.

TABLE 9

Bacterial counts in the salad Dressing.

| Designation | Time (days) | | |
|---|---|---|---|
| | T-0[a] | T-2 | T-10 |
| A | <$10^{2b}$ | <$10^3$ | $10^8$ |
| B | $10^2$ | <$10^2$ | $10^5$ |
| C | $10^2$ | <$10^2$ | $10^3$ |

[a]Time (days)
[b]Bacterial Counts (cfu/g) *Lactobacillus* sp. spoilage agents

The results show that LL-1 was very effective in inhibiting the growth of the lactic bacteria naturally present in the salad dressing.

The bacteriocin LL-1 was stable in various environments. The bacteriocin was effective in reducing the initial contaminant bacteria load and maintaining this protection over a period of several days. The same results can be achieved in various food systems such as gravies, meats, vegetables and the like, which can be raw or cooked, and particularly coleslaw, macaroni salad, potato salad and sausages. The bacteriocin is particularly effective where raw foods are mixed with other ingredients which promote the growth of Gram-positive bacteria naturally present on food. The bacteriocin can be effective on such items as bandages, sanitary napkins and ointments (liquids and powders) used for wound healing. In general the bacteriocin can also be useful in the form of ointments (liquids, or powders) as disinfectant for animate and inanimate objects where *Staphylococcus aureus* is a problem. The bacteriocin can also be used to treat wounds in mammals which can be infected with Gram-positive bacteria.

It is intended that the foregoing description be only illustrative of the present invention and that the present invention be limited only by the hereinafter appended claims.

We claim:
1. A purified bacteriocin produced by a Lactococcus which comprises:
    a protein having a molecular weight of about 6000 daltons, which is inactivated by protease V and not inactivated by alpha-chymotrypsin, trypsin, lipase, pepsin and lysozyme, inhibits growth of bacteria selected from the group consisting of *Staphylococcus aureus, Staphylococcus epidermidis, Staphylococcus carnosus, Pediococcus pentosaceus, Pediococcus acidilactici, Lactococcus cremoris, Lactococcus lactis, Leuconostoc mesenteroides, Lactobacillus bulgaricus,*

*Lactobacillus fermentum, Lactobacillus bifermentans* and *Lactobacillus plantarum* and has a pH for inhibition between about pH 2 and 8 wherein the purified bacteriocin has a high pressure liquid chromatographic amino acid profile as shown in FIG. 1 as a result of hydrolysis of the bacteriocin to produce the amino acids and labeling of the amino acids with phenyl isothiocyanate, wherein the ratio of amino acids to glutamic acid are as follows:

| Amino Acid Ratio to glutamic acid | |
|---|---|
| Aspartic acid | 0.42 |
| Glutamic acid | 1.0 |
| Serine | 0.35 |
| Glycine | 0.83 |
| Histidine | 0.16 |
| Arginine | 0.35 |
| Threonine | 0.34 |

-continued

| Amino Acid Ratio to glutamic acid | |
|---|---|
| Alanine | 0.76 |
| Proline | 0.48 |
| Tyrosine | 0.19 |
| Valine | 0.43 |
| Methionine | 0.14 |
| Cysteine | 0.12 |
| Isoleucine | 0.27 |
| Leucine | 0.64 |
| Phenylalanine | 0.19 |
| Lysine | 0.50 | wherein the bacteriocin is produced by *Lactococcus lactis* NRRL-B-18535 in a culture medium.

wherein the bacteriocin is produced by *Lactococcus lactis* NRRL-B-18535 in a culture medium.

* * * * *

UNITED STATES PATENT AND TRADEMARK OFFICE
CERTIFICATE OF CORRECTION

PATENT NO. : 5,877,272
DATED : March 2, 1999
INVENTOR(S) : Peter A. Vandenbergh, Shirley A. Walker and Blair S. Kunka It is certified that error appears in the above-indentified patent and that said Letters Patent is hereby corrected as shown below:

Column 7, line 56, "bcteriocin" should be --bacteriocin--.

Column 12, line 13, (Claim 1) "wherein the bacteriocin is produced by *Lactococcus lactis*, NRRL-B-18535 in a culture medium." (first occurrence), should be deleted.

Signed and Sealed this

Twenty-sixth Day of October, 1999

Attest:

Q. TODD DICKINSON

*Attesting Officer*   *Acting Commissioner of Patents and Trademarks*